(12) United States Patent
McLevish

(10) Patent No.: US 9,408,960 B2
(45) Date of Patent: Aug. 9, 2016

(54) PARTIAL RADIAL HEAT EXCHANGER AND OXYGENATOR

(71) Applicant: Medtronic, Inc., Minneapolis, MN (US)

(72) Inventor: Alford McLevish, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 281 days.

(21) Appl. No.: 14/134,641

(22) Filed: Dec. 19, 2013

(65) Prior Publication Data

US 2015/0174311 A1   Jun. 25, 2015

(51) Int. Cl.
*A61M 1/16* (2006.01)
*A61M 1/32* (2006.01)
*B21D 53/02* (2006.01)

(52) U.S. Cl.
CPC ............... *A61M 1/32* (2013.01); *A61M 1/1698* (2013.01); *B21D 53/027* (2013.01); *A61M 2205/3372* (2013.01); *A61M 2205/366* (2013.01); *Y10T 29/49362* (2015.01)

(58) Field of Classification Search
CPC ............... A61M 1/1698; A61M 1/32; A61M 2205/3372; A61M 2205/336; B21D 53/027; Y10T 29/49362
See application file for complete search history.

(56) References Cited

U.S. PATENT DOCUMENTS

| 4,715,953 | A | | 12/1987 | Leonard | |
|---|---|---|---|---|---|
| 5,225,161 | A | * | 7/1993 | Mathewson et al. | 422/46 |
| 5,395,468 | A | | 3/1995 | Juliar | |
| 5,817,279 | A | * | 10/1998 | Eilers et al. | 422/46 |
| 2010/0269342 | A1 | | 10/2010 | Carpenter | |
| 2010/0272604 | A1 | | 10/2010 | Carpenter | |
| 2010/0274170 | A1 | | 10/2010 | Carpenter | |
| 2012/0197363 | A1 | * | 8/2012 | Cloutier et al. | 607/106 |
| 2012/0277653 | A1 | | 11/2012 | Olsen | |
| 2013/0209314 | A1 | | 8/2013 | Roller | |
| 2013/0231601 | A1 | | 9/2013 | Gloss | |

FOREIGN PATENT DOCUMENTS

WO   WO9725080   7/1997

* cited by examiner

*Primary Examiner* — Philip R Wiest
*Assistant Examiner* — Benjamin Klein

(57) ABSTRACT

Methods of making a combination heat exchanger and oxygenator. A heat transfer tubing is wound about a core and a potting compound is applied to a portion of the wound tubing. The potting compound solidifies to form a potting structure defining an internal face substantially parallel with a longitudinal axis of the core. The assembly is cut along a line passing through the potting structure to define a core assembly having a cut face substantially parallel with the axis. The cut tubing forms a plurality of capillary tubes, each terminating at opposing, first and second ends, and each extending about the core along an arc angle of less than 360 degrees. An oxygenator bundle is formed as part of the core assembly and includes a plurality of gas exchange fibers. The core assembly is disposed within a housing having a blood inlet and a blood outlet.

20 Claims, 14 Drawing Sheets

PARTIAL RADIAL HEAT EXCHANGER AND OXYGENATOR

BACKGROUND

The present disclosure relates to extracorporeal blood circuit devices, and related methods of manufacture. More particularly, it relates to devices for regulating the temperature of and oxygenating a patient's blood during surgery.

An extracorporeal blood circuit is commonly used during cardiopulmonary bypass to withdraw blood from the venous portion of the patient's circulation system and return the blood to the arterial portion. The extracorporeal blood circuit typically includes a venous drainage line, a venous blood reservoir, a blood pump, an oxygenator, a heat exchanger, one or more filters, and blood transporting tubing, ports, and connection pieces interconnecting the various components.

Blood oxygenators are disposable components of the extracorporeal circuit and are used to oxygenate blood. In general terms, the oxygenator takes over, either partially or completely, the normal gas exchange function of the patient's lungs. The oxygenator conventionally employs a microporous membrane or bundle comprised of thousands of microporous or semi-permeable hollow fibers (or "gas exchange fibers"). Blood flow is directed around the outside surfaces of the gas exchange fibers. Concurrently, an oxygen-rich gas mixture is passed through the fiber lumens. Due to the relatively high concentration of carbon dioxide in blood arriving from the patient, carbon dioxide is transferred from the blood, diffusing across the microporous fibers and into the passing stream of oxygenating gas. At the same time, oxygen is transferred from the oxygenating gas, diffusing across the fibers and into the blood. The oxygen content of the blood is thereby raised, and the carbon dioxide content is reduced.

A well-accepted technique for forming a hollow fiber oxygenator bundle is to first spirally wind a length of continuous gas exchange tubing about an internal supporting core in a back-and-forth manner to generate a wound bundle, as described for example in U.S. Pat. No. 4,975,247. Upon completion of the winding process, the wound bundle has a generally cylindrical shape defining a longitudinal axis and opposing ends. The continuous gas exchange tubing traverses multiple, spiral winds of the wound bundle. A potting compound or epoxy is then applied to and solidified at each of the opposing ends. A cut is formed through a thickness of the potting compounds and the tubing at each of the opposing ends (perpendicular to the longitudinal axis), dividing the continuous gas exchange tubing into a series of discrete gas exchange fibers. Each gas exchange fiber traverses a single spiral wind path from one cut end to the opposite cut end, and the lumen of each fiber is open at the opposing ends.

To complete the oxygenator device, the oxygenator bundle is sealed in a side wall of a housing that is then fitted with skirted end caps. A gas inlet and a gas outlet are provided by the housing (normally at the end caps, respectively), and are fluidly connected to the gas exchange fiber open ends. The oxygenating gas enters the device through the gas inlet, passes through the lumens of the hollow fibers, and exits the device through the outlet. More particularly, oxygenating gas supplied to each fiber at the first end of the oxygenator bundle flows along a spiral path of the corresponding lumen, experiencing several 360 degree rotations about the longitudinal axis. FIG. 1 illustrates this arrangement in simplified form, showing an oxygenator bundle 10 having a gas exchange fiber 12 traversing multiple revolutions about the longitudinal axis L. Blood flow through the annular bundle of gas exchange fibers can be in various directions such as radially outward, axial, circumferential, etc. With radially outward flow designs, U.S. Pat. No. 5,462,619 describes an improved winding technique that provides desired pressure drops and minimal clotting risks by a graduated packing fraction.

Regardless of the exact format, typically the patient's blood is continuously pumped through a heat exchanger component prior to interfacing with the oxygenator. The heat exchanger core is generally made of metal or plastic tubes that are able to transfer heat effectively to blood coming into contact with the metal or plastic. With extracorporeal blood circuit applications, the heat exchanger core can be formed by a multiplicity or bundle of capillary tubes. The heat transfer capillary tubes are often collectively provided as pre-formed mat, knitted, woven or otherwise held together with threads or stitching forming the warp of the mat. To assemble the heat exchanger, the mat is typically wrapped or rolled around a core or mandrel. As the mat is continuously wrapped about the mandrel, the mat winds onto itself, resulting in a series of radially increasing layers. The capillary tubes of the mat are conventionally "biased" so that the tubes are not parallel with a width of the mat. Two layers of the mat with opposite bias angles can be simultaneously wound on the core to prevent the capillary tubes of subsequent layers from nesting in the gaps between the capillary tubes of a preceding layer as the mat is wrapped onto itself. Regardless, a suitable heat transfer fluid, such as water, is pumped through the tube lumens while blood flows about the tube exteriors, separate from the blood but in heat transfer relationship therewith. The water is either heated or cooled externally of the heat exchanger, with the heat exchanger functioning to control or adjust the temperature of the blood in a desired direction.

Many commercially available oxygenator devices incorporate both a heat exchanger core and a membrane-type oxygenator bundle in a common housing. Heat exchangers provided in the same housing as a blood oxygenator are subject to a number of design constraints. The heat exchanger should be compact due to physical space limitations in the operating room environment. Also, small size is important in minimizing the internal priming volume of the blood oxygenator due to the high costs and limited supply of blood. However, the heat exchanger must be large enough to provide an adequate volumetric flow rate to allow proper temperature control and oxygenation. On the other hand, blood flow rate or flow resistance inside the blood oxygenator must not be excessive since the cells and platelets in the human blood are delicate and can be traumatized if subjected to excessive shear forces resultant from turbulent flow.

To address the above (and other) concerns, more recent combination heat exchanger and oxygenator devices have the oxygenator bundle wound or formed directly over the heat exchanger core. With some combination heat exchanger or oxygenator devices, the heat exchanger capillary tube mat is wrapped about a mandrel, followed by formation of the gas exchange tubing bundle (e.g., the gas exchange tubing is spirally wound over the wrapped capillary tube mat). Opposing ends of the so-assembled bundles are then potted and cut to generate openings to the lumens of the capillary tubes and the gas exchange fibers. Top and bottom end caps, each carrying both a heat exchanger port and an oxygenator port, are assembled over the cut bundle assembly. During use, the oxygenating medium follows a spiral path through the gas exchange fibers as described above; the heat transfer fluid similarly flows spirally through individual capillary tubes.

While highly viable, wound gas exchange fiber and capillary mat-based integrated bundle assemblies have possible drawbacks. For example, capillary tube mats are expensive due to the complexities of the knitting or weaving process.

Further, the size, bias, materials, spacing, etc., of the capillary tubes in the mat is fixed, such that possible benefits available with varying one or more of these parameters is unavailable. Also, the relatively long spiral flow path of the heat transfer fluid and the gas exchange medium may not be optimal. Also, multiple additional sealing members are required to ensure that the blood, oxygenator medium, and heat transfer fluid do not co-mingle. Any improvements would be well received.

SUMMARY

Some aspects in accordance with principles of the present disclosure relate to an apparatus for oxygenating and controlling temperature of blood in an extracorporeal circuit. The apparatus includes a housing, a core, a heat exchanger bundle, and an oxygenator bundle. The housing provides a blood inlet and a blood outlet. The core is disposed within the housing and defines a longitudinal axis. The heat exchanger bundle includes a plurality of heat transfer capillary tubes arranged directly over the core. Each of the capillary tubes terminates at opposing first and second ends, and each extends about the core to define an arc relative to the longitudinal axis. The arc of each of the capillary tubes has an arc angle of less than 360 degrees. The oxygenator bundle includes a plurality of gas exchange fibers arranged directly over the heat exchanger bundle. With this construction, the apparatus is configured to establish a blood flow path from the blood inlet to the blood outlet that passes radially through the heat exchanger bundle and the oxygenator bundle. In some embodiments, each of the gas exchange fibers terminates at opposing first and second ends, and extends about the heat exchanger bundle to define an arc relative to the longitudinal axis having an arc angle of less than 360 degrees. In related embodiments, a potting structure encompass the ends of each of the heat transfer capillary tubes and of the gas exchange fibers, with the heat transfer fluid and the oxygenation medium traversing through each of the corresponding lumens, respectively, by less than 360 degrees.

Other aspects in accordance with principles of the present disclosure relate to a method of making an apparatus for oxygenating and controlling temperature of blood in an extracorporeal circuit. The method includes winding at least one length of continuous heat transfer tubing about a core that otherwise defines a longitudinal axis to form a heat exchanger precursor bundle. A potting compound is applied to a portion of the heat exchanger precursor bundle to provide an intermediate core assembly having a length direction aligned with the longitudinal axis. The solidified potting structure extends through the heat exchanger precursor bundle in a plane substantially parallel with the longitudinal axis. The intermediate core assembly is then cut along a cut line passing through the potting structure in the length direction to define a core assembly having a cut face. In this regard, the step of cutting transforms the continuous heat transfer tubing into a plurality of capillary tubes each terminating at opposing first and second ends, and each extending about the core to define an arc relative to the longitudinal axis. The arc of each of the capillary tube has an arc length of less than 360 degrees. The first and second ends of each of the capillary tubes are open to the corresponding lumen at the cut face to collectively define a heat exchanger bundle. An oxygenator bundle is formed as part of the final core assembly and includes a plurality of gas exchange fibers arranged directly over the heat exchanger bundle. Finally, the core assembly is disposed within a housing that otherwise provides a blood inlet and a blood outlet. In some embodiments, a continuous length of gas exchange tubing is wound over the heat exchanger precursor bundle to form an oxygenator precursor bundle prior to the cutting step, with the potting compound being applied to both the heat exchanger precursor bundle and the oxygenator precursor bundle; in related embodiments, the step of cutting the intermediate core assembly transforms the gas exchange tubing into the plurality of gas exchange fibers each revolving about the longitudinal axis by less than 360 degrees.

DETAILED DESCRIPTION

Figure 1:
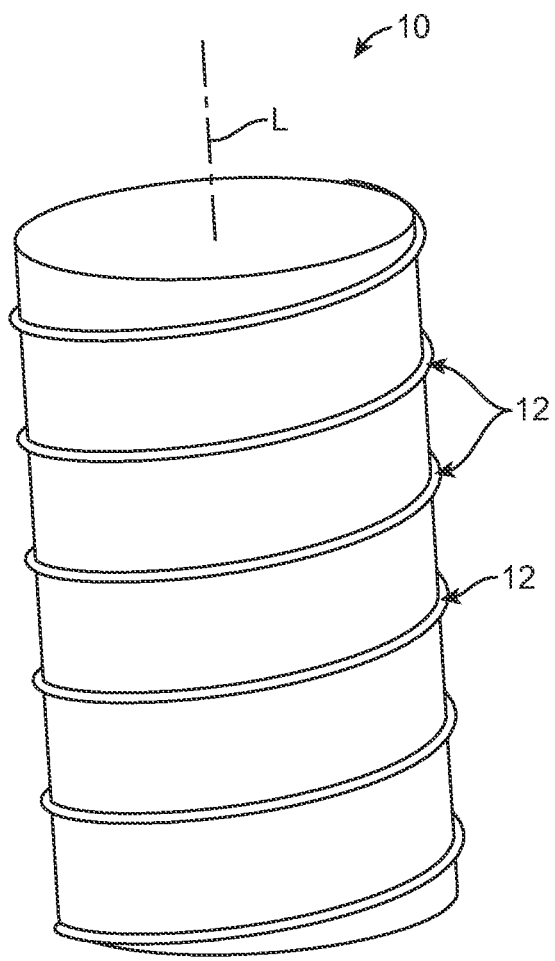
FIG. 1 is a simplified perspective view of a prior art oxygenator bundle.
Figure 2A:
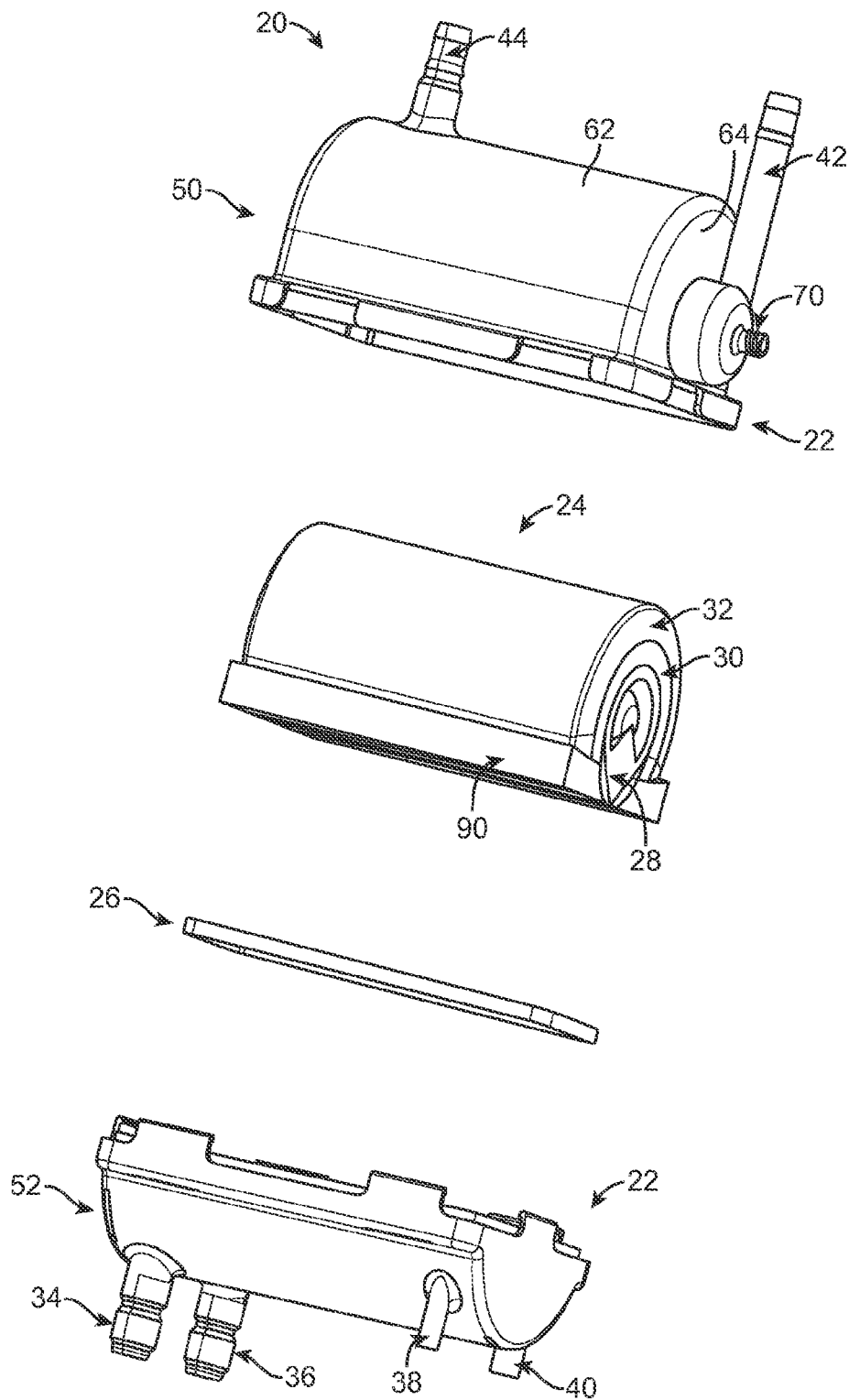
FIG. 2A is a perspective, exploded view of a combination oxygenator and heat exchanger apparatus in accordance with principles of the present disclosure.
Figure 2B:
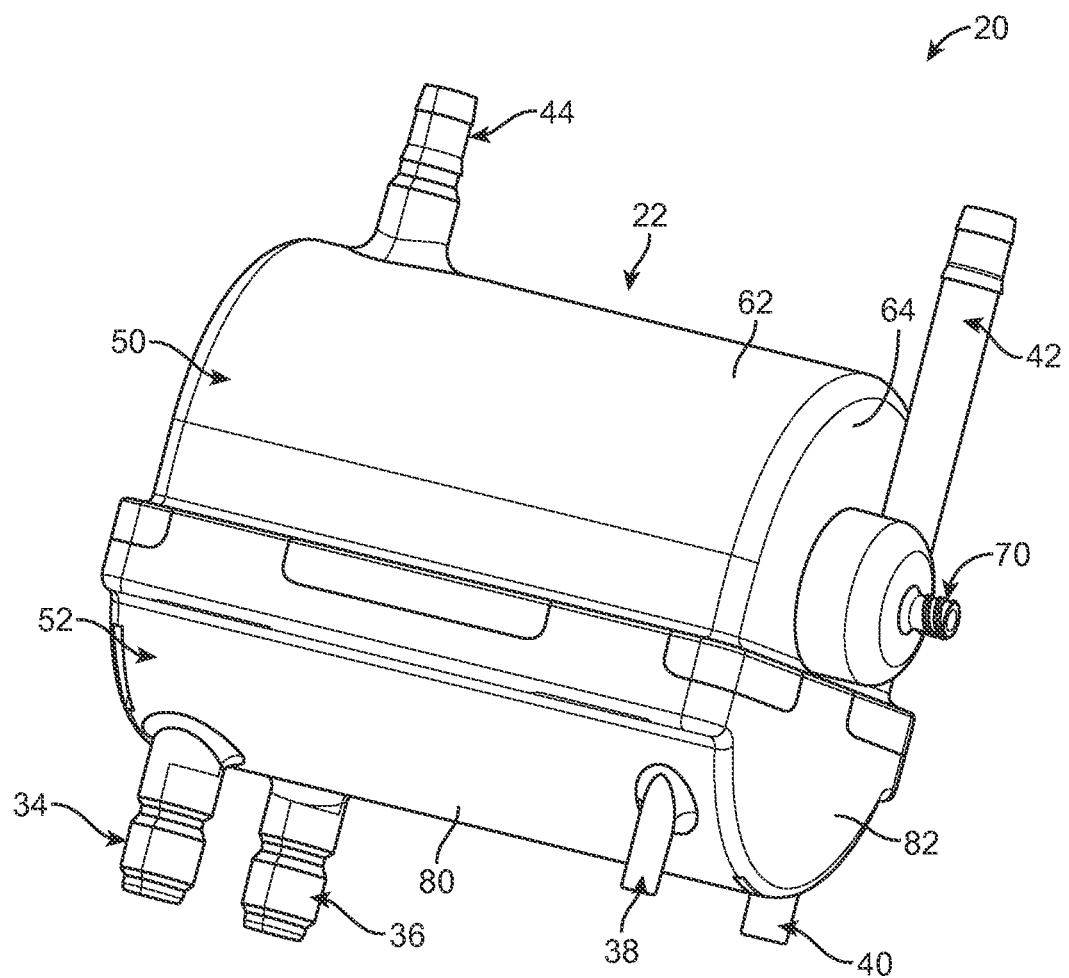
FIG. 2B is a perspective view of the apparatus of FIG. 2A upon final assembly.

One embodiment of an apparatus 20 in accordance with principles of the present disclosure and useful for oxygenating and controlling temperature of blood in an extracorporeal blood circuit is shown in FIGS. 2A and 2B. The apparatus 20 includes a housing 22, a core assembly 24, and a separator 26. Details on the various components are provided below. In general terms, however, the core assembly 24 includes a core or mandrel 28, a heat exchanger bundle 30, and an oxygenator bundle 32. The separator 26 is mounted to the core assembly 24 to fluidly isolate the heat exchanger bundle 30 from the oxygenator bundle 32. The core assembly 24 and the separator 26 are disposed within the housing 22, with the housing 22 providing heat transfer inlet and outlet ports 34, 36 for fluidly communicating with the heat exchanger bundle 30, gas exchange inlet and outlet ports 38, 40 for fluidly communicating with the oxygenator bundle 32, and blood inlet and outlet ports 42, 44. A blood flow path is defined from the blood inlet 42 to the blood outlet 44, with a temperature of the blood being controlled along the heat exchanger bundle 30 followed by oxygenation at the oxygenator bundle 32. As described below, the core assembly 24 is configured such that the heat transfer fluid flows a relative short distance along the heat exchanger bundle 30, resulting in a more efficient heat exchange; in some embodiments, the gas exchange path along the oxygenator bundle 32 is optionally relatively short, resulting in a beneficial decrease in gas residence time.

The housing 22 can include various components separately formed and subsequently assembled to one another, such as a first housing portion 50 and a second housing portion 52. The first portion 50 is generally configured to receive the core assembly 24 (FIG. 2A), and can serve as case component. The second portion 52 is configured for sealed assembly to the first portion 50, and can be akin to a cap that incorporates various features establishing desired flow paths. The housing portions 50, 52 can be made of various medical grade materials, such as polycarbonate or transparent polycarbonate.

Figure 3A:
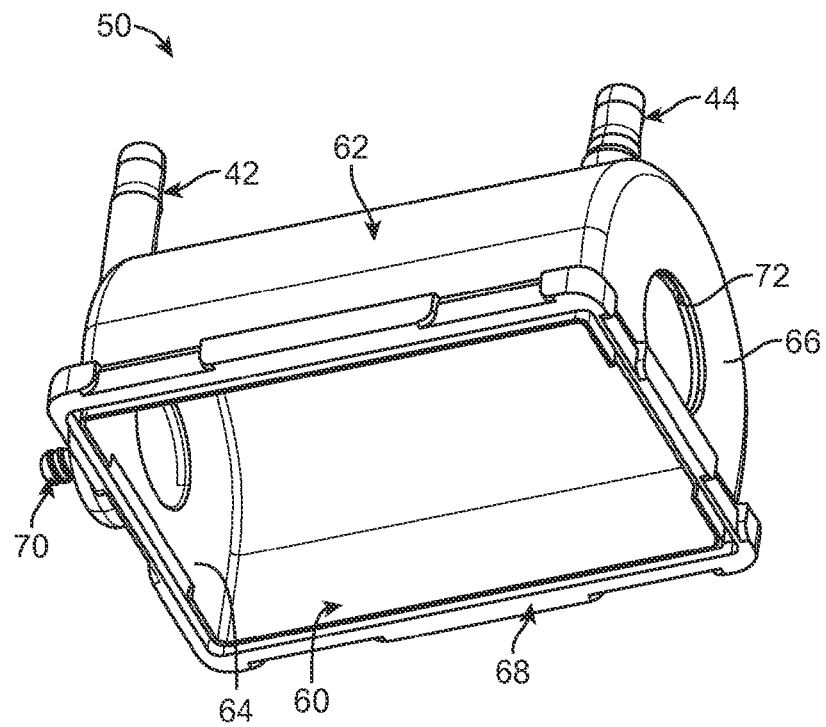
FIG. 3A is a bottom perspective view of a first portion of a housing useful with the apparatus of FIG. 2A.

With additional reference to FIG. 3A that otherwise illustrates the first housing portion 50 from another vantage point, the first housing portion 50 generally defines a chamber 60 via a side wall 62. The side wall 62 forms the chamber 60 to have a semi-cylindrical shape, generally sized and shaped in accordance with the size and shape of the core assembly 24. The chamber 60 is bounded at opposite sides by end walls 64, 66, with the walls 62-66 collectively terminating at a flange 68. The flange 68 circumscribes an opening to the chamber 60. As shown, the first housing portion 50 forms or carries the blood inlet port 42 and the blood outlet port 44. With some embodiments, the blood inlet port 42 is arranged to direct incoming blood flow along a longitudinal axis of the first housing portion 50, whereas the blood outlet port 44 receives blood from the chamber 60 in a radial direction. An air purge port 70 is optionally formed at the first end wall 64 and is fluidly open to the chamber 60. In some embodiments, a hole 72 is formed in the second end wall 66. Where provided, the hole 72 can facilitate molding of the first housing portion 50, and optionally provides a convenient handling feature as described below.

Figure 3B:
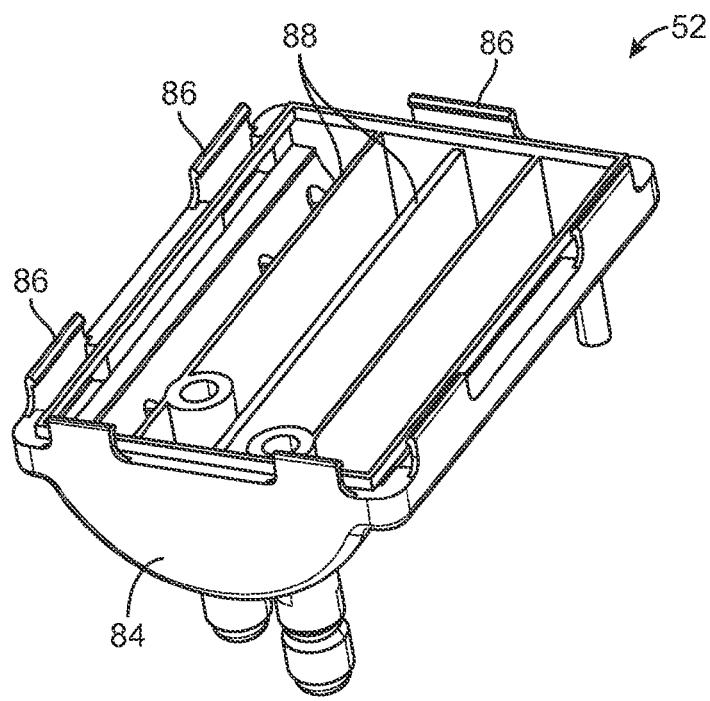
FIG. 3B is a top perspective view of a second housing portion useful with the apparatus of FIG. 2A.

With additional reference to FIG. 3B, the second housing portion 52 includes a side wall 80 (primarily hidden in FIG. 3B), end walls 82, 84, and one or more clips 86. The side wall 80 can define a variety of shapes, and in some embodiments generally follows the rounded shape of the first housing portion side wall 62 so as to provide an aesthetically-pleasing appearance to the housing 22 upon final assembly. The clips 86 are configured in accordance with first housing portion flange 60 for mated assembly therebetween. In some embodiments, the housing portions 50, 52 are constructed to provide a fluid-tight seal upon final assembly, either alone or in combination with other components such as a gasket (not shown), adhesive, etc. Regardless, in some embodiments, the second housing portion 52 includes internal support walls 88 that are configured to support the core assembly 24 (FIG. 2A) upon final assembly as described below. Finally, the second housing portion 52 forms or carries the heat transfer inlet and outlet ports 34, 36 as well as the gas exchange inlet and outlet ports 38, 40.

Returning to FIG. 2A, the core 28, heat exchanger bundle 30, and oxygenator bundle 32 components of the core assembly 24 can be provided in a variety of manners, and the core assembly 24 can further include a solidified potting structure 90. Although the core assembly 24 can be provided as a singular assembly in which the heat exchanger bundle 30 (and optionally the oxygenator bundle 32) is integrally formed on the core 28, FIG. 4 provides an exploded view of one embodiment of the core assembly 24 for ease of understanding.

Figure 5A:
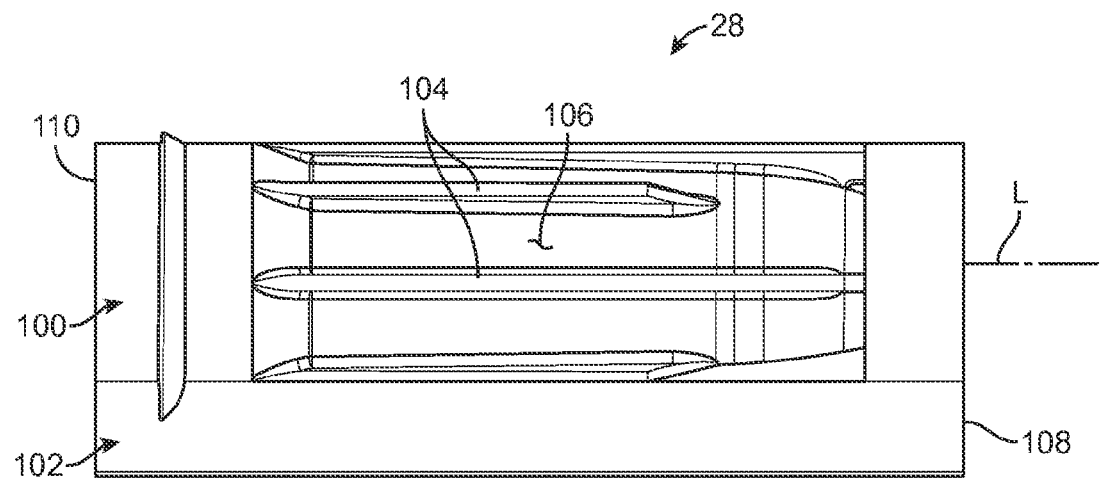
FIG. 5A is a side view of a core component of the core assembly of FIG. 4.
Figure 5B:
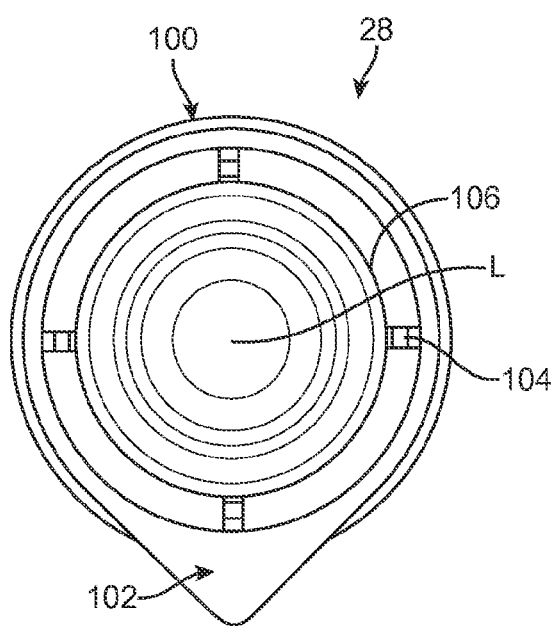
FIG. 5B is a front end view of the core of FIG. 5A.

The core 28 can assume a variety of forms, and is generally an elongated, cylindrically-shaped body. In some embodiments, and with additional reference to FIGS. 5A and 5B, the core 28 defines a circular region 100 and a shoulder region 102. The circular region 100 defines a central longitudinal axis L. The shoulder region 102 projects radially from a perimeter of the circular region 100 (i.e., radial to the longitudinal axis L), and can have the tapered shape shown. Where provided, the shoulder region 100 extends along an entire length of the circular region 100, with the circular region 100 optionally forming a series of circumferentially spaced ribs 104 projecting from an outer surface 106. Where provided, a spacing between the ribs 104 serve as flow paths for blood along the core 28, as the blood interfaces with the core 28 at an inlet side 108. In some embodiments, the circular region 100 can be a hollow body that is closed at the inlet side 108 and open at an opposite base side 110. Alternatively, the core 28 can be a solid body, may or may not include the shoulder region 102 and/or the ribs 104, and can optionally incorporate other features (e.g., flanges, recesses, etc.). In yet other embodiments, the core 28 can incorporate an opening at the inlet side 108 and is configured to facilitate blood flow in a radial direction through holes in the outer surface 106.

Figure 4:
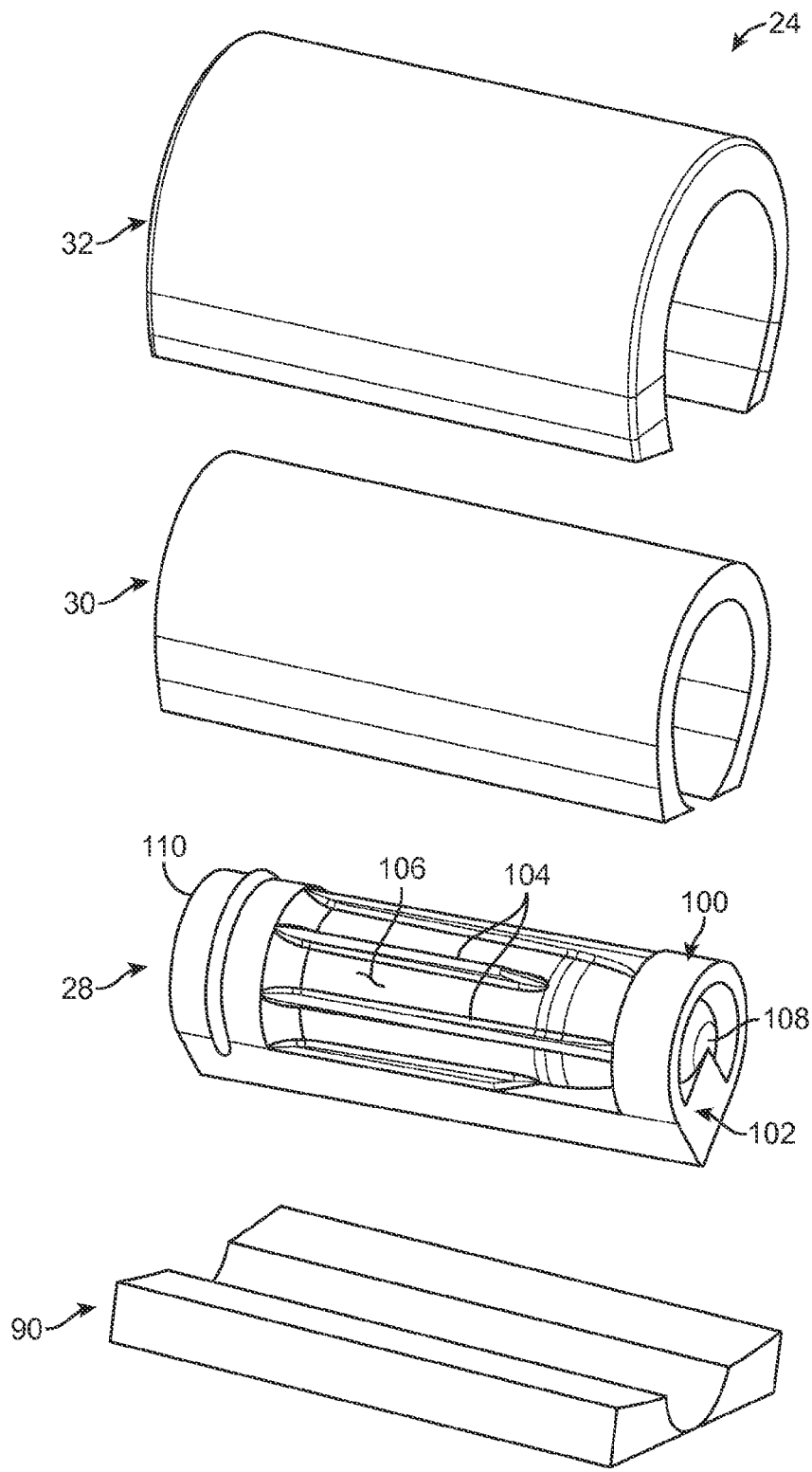
FIG. 4 is an exploded view of a core assembly useful with the apparatus of FIG. 2A.

With specific reference to FIG. 4, the heat exchanger bundle 30 includes a plurality of micro-diameter capillary tubes or hollow heat transfer elements (not shown individually), which may be fibers, tubes, capillaries, compartments, etc. In some embodiments, the heat transfer capillary tubes are formed of a thermally conductive polymer or metal, such as polyethylene terephthalate (PET) or polyurethane. The capillary tubes are independent of one another and are not interconnected (apart from the potting structure 90) by threads or stitching. In general terms, the purpose of the heat transfer capillary tubes of the heat exchanger bundle 30 is to transfer heat to or from an exchange fluid running through lumens of the tubes to or from the blood that flows between the heat transfer capillary tubes.

The oxygenator bundle 32 is generally disposed about the heat exchanger 30, and includes a plurality of gas exchange fibers (not shown individually). The gas exchange fibers are made of semi-permeable membrane including micropores. In some embodiments, the gas exchange fibers are hollow microporous polypropylene-based fibers, but other materials are also contemplated by the present disclosure. Any suitable microporous fiber may be used as the gas exchange fibers or elements of the oxygenator bundle 32.

Figure 6A:
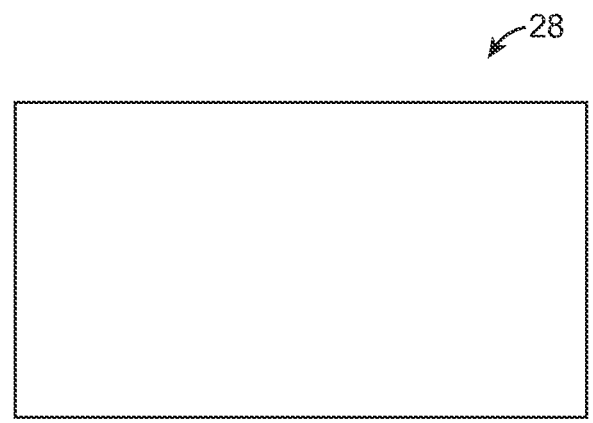
FIG. 6A is a simplified side view of a core useful with the apparatus of FIG. 2A.
Figure 6B:
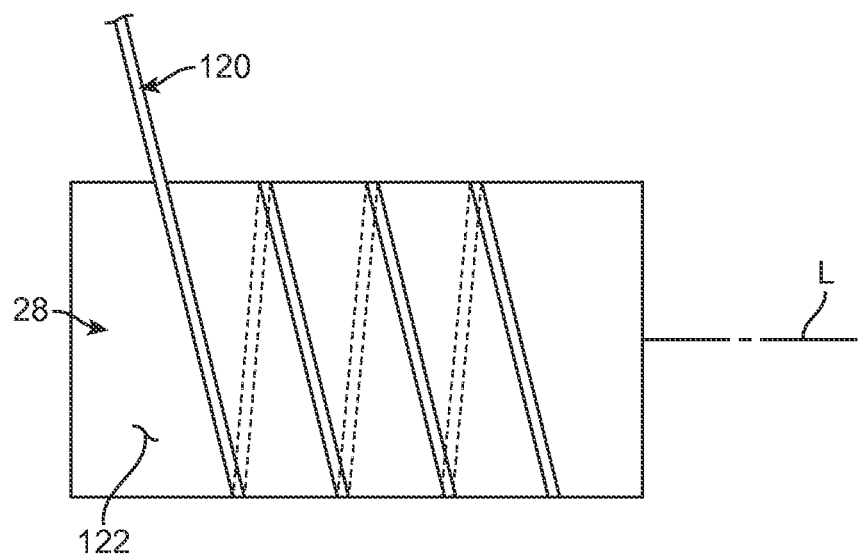
FIG. 6B illustrates winding of a heat transfer tubing about the core of FIG. 6A.

In some embodiments, construction of the core assembly 24 includes forming the heat exchanger bundle 30 directly on the core 28. For example, FIG. 6A illustrates the core 28 in highly simplified form, and prior to formation of the heat exchanger bundle 30 (FIG. 2A) or the oxygenator bundle 32 (FIG. 2A). At least one continuous length of heat transfer tubing 120 (a diameter of which is exaggerated in the views for ease of understanding) is spirally wound about an exterior face 122 of the core 28 as shown in FIG. 6B. As a point of reference, the heat transfer tubing 120 is later cut (as described below) to generate a multiplicity of the heat transfer capillary tubes of the heat exchange bundle 30 (FIG. 4). Thus, the heat transfer tubing 120 can assume any of the forms described above with respect to the heat transfer capillary tubes, it being understood that in accordance with the nomenclature of the present disclosure, the "tubing" is subsequently converted into the "capillary tubes". FIG. 6B represents an initial stage of the winding process, with the heat transfer tubing 120 being continuously wound about the exterior face 122 in a helical-like or spiral-like manner relative to the longitudinal axis L. In some embodiments, the winding operation can be performed using winding apparatus that simultaneously applies several heat transfer tubings 120 side-by-side (e.g., as a ribbon).

Figure 6C:
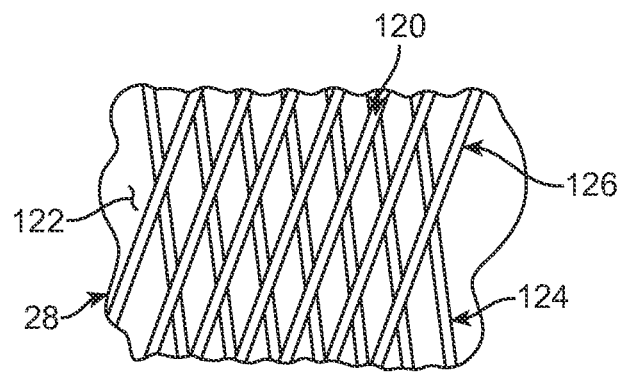
FIG. 6C is an enlarged view of a portion of the arrangement of FIG. 6B following additional winding of the heat transfer tubing.

The winding angle and/or tension during the winding process can be manipulated to affect a desired packing fraction and/or layer to layer arrangement of the wound tubing 120. For example, and as generally reflected in FIG. 6B, the heat transfer tubing 120 is arranged at a slight angle relative to the longitudinal axis L as the heat transfer tubing 120 is wound from right-to-left (relative to the orientation of FIG. 6B) during a first traverse along a length of the core 28. As the winding is subsequently traversed in the opposite direction (left-to-right), the angle of the tubing 120 can be altered relative to the longitudinal axis L to prevent nesting of the heat transfer tubing 120 from layer-to-layer. FIG. 6C illustrates a subsequent stage of winding of the tubing 120 over the core exterior face 122. The winding establishes a first layer 124 and a second layer 126. As shown, the tubing 120 is arranged along the first layer 124 at an angle that differs from that established along the second layer 126. Portions of the heat transfer tubing 120 laid down during formation of the second layer 126 contact the tubing 120 of the first layer 124 at certain cross over points. Except for these cross over points at which there is tubing-to-tubing contact with the first layer 124, the tubing 120 laid down during the second traverse come into direct contact with the core exterior face 122.

Figure 6D:
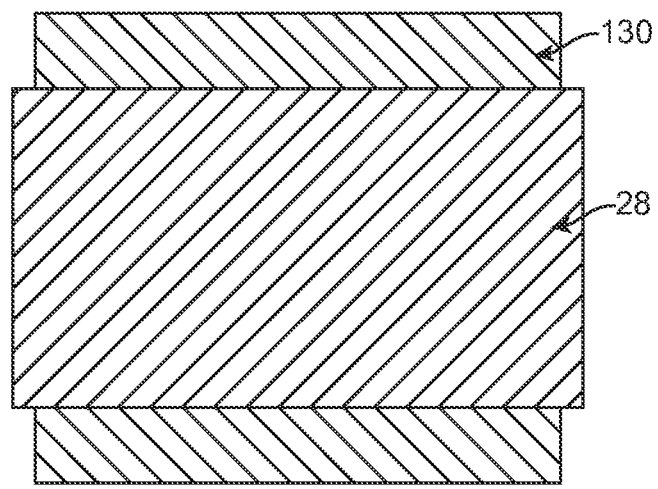
FIG. 6D is a simplified cross-sectional view of a heat exchanger precursor bundle formed by successive windings of the tubing of FIG. 6B onto the core of FIG. 6A.

Following multiple, back-and-forth cycling or winding of the heat transfer tubing 120 (and thus formation of multiple layers of the tubing 120), a heat exchanger precursor bundle 130 is formed over the core 28 as shown in the highly simplified cross-sectional representation of FIG. 6D. As a point of reference, the heat exchanger precursor bundle 130 is subjected to subsequent processing (described below) including a cutting operation that transitions the precursor bundle 130 to the final heat exchanger bundle 30 of FIG. 4. In other words, the "heat exchanger precursor bundle" is in reference to the wound heat transfer tubing 120 (FIG. 6B) prior to cutting, whereas the final "heat exchanger bundle" is in reference to a cut format in which the tubing 120 has been converted into a multiplicity of individual heat transfer capillary tubes.

Figure 7A:
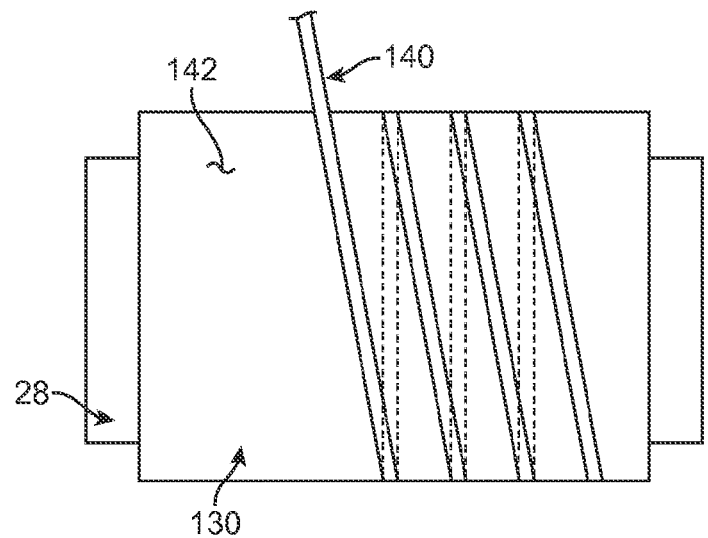
FIGS. 7A and 7B are simplified illustrations of an oxygenator precursor bundle being formed onto the heat exchanger precursor bundle of FIG. 6D.
Figure 7B:
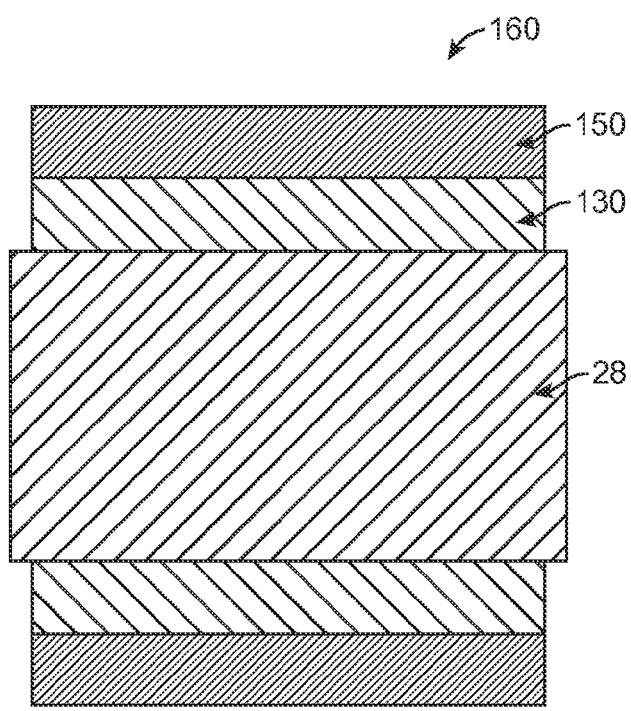

Construction of the core assembly 24 (FIG. 4) can then include winding at least one continuous length of gas exchange tubing 140 over an exterior face 142 of the heat exchanger precursor bundle 130 as reflected by the highly simplified illustration of FIG. 7A in which a diameter of the gas exchange tubing 140 is exaggerated for ease of understanding. To clarify, the gas exchange tubing 140 will subsequently be cut (as described below) to generate a multiplicity of the gas exchange fibers of the oxygenator bundle 32 (FIG. 4) such that the gas exchange tubing 140 can have any of the constructions described above with respect to the gas exchange fibers. Winding of gas exchange tubing 140 can be performed in manner similar to the above descriptions relative to formation of the heat exchanger precursor bundle 130 (e.g., the winding angle and/or tension during the spiral winding process can be manipulated to affect a desired packing fraction), with the gas exchange tubing 140 being spirally wound over the heat exchanger precursor bundle 130 in multiple, back-and-forth traverses or passes. Upon completion of winding, an oxygenator precursor bundle 150 is directly formed over the heat exchanger precursor bundle 130 as shown in FIG. 7B. As a point of reference, the oxygenator precursor bundle 150 is subjected to subsequent processing (described below) that transitions the oxygenator precursor bundle 150 to the final oxygenator bundle 32 of FIG. 4.

Figure 8A:
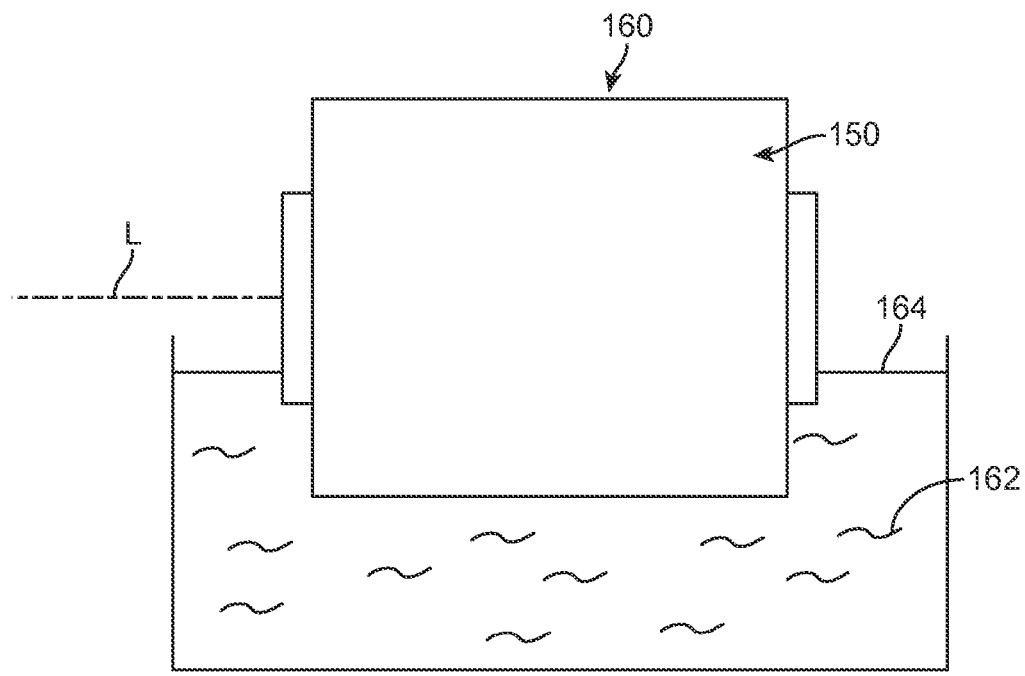
FIGS. 8A-9B illustrate additional manufacturing steps in forming the core assembly of FIG. 2A in accordance with the principles of the present disclosure.
Figure 8B:
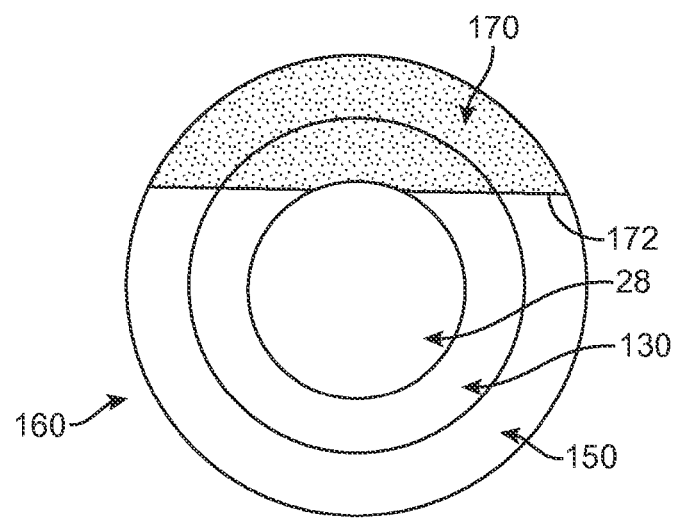

The core 28, the heat exchanger precursor bundle 130 and the oxygenator precursor bundle 150 collectively define a precursor bundle assembly 160 that is then partially submerged within or treated with a potting compound (in a liquid state) 162 as shown in FIG. 8A. As is generally known in the art, the fiber/capillary tube potting process introduces a potting material (e.g., polyurethane) by centrifuging and is reacted in situ. The liquid potting compound 162 is applied lengthwise to the precursor bundle assembly 160. For example, the liquid potting compound 162 can be held within a basin to define an upper surface or level 164. The precursor bundle assembly 160 is partially submerged beneath the upper level 164 such that the longitudinal axis L is substantially parallel (e.g., within 10% of a truly parallel relationship) with the upper level 164. With this orientation, the liquid potting compound 162 is applied to an entire length of the precursor bundle assembly 160, and seeps or leaches into a thickness of the heat exchanger precursor bundle 130 (FIG. 7B) and the oxygenator precursor bundle 150 up to the upper level 164. More particularly, FIG. 8B schematically illustrates a solidified potting compound 170 (shown by stippling in the view of FIG. 8B) applied to the precursor bundle assembly 160, terminating at an edge 172 within a thickness of the assembly 160.

Figure 9A:
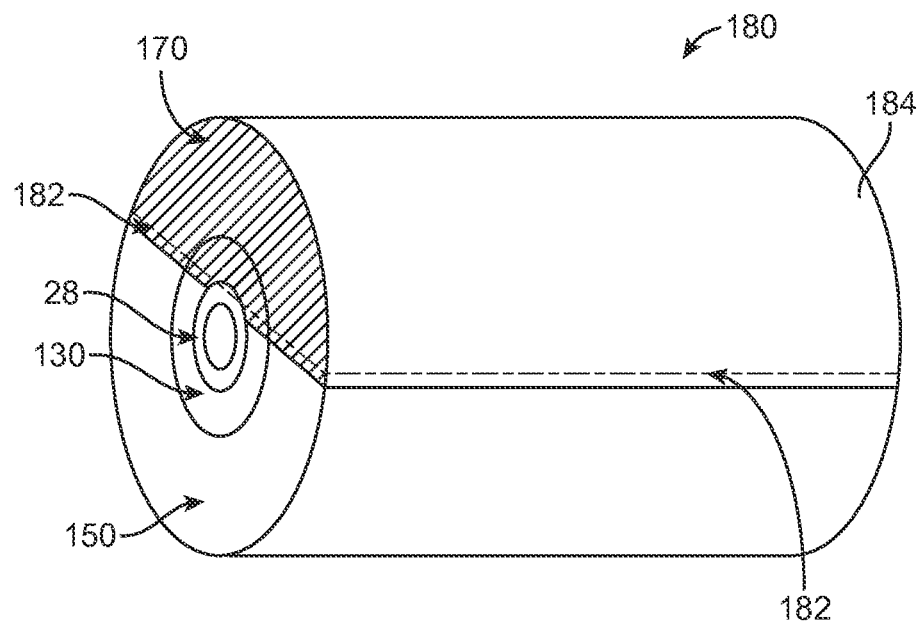
Figure 9B:
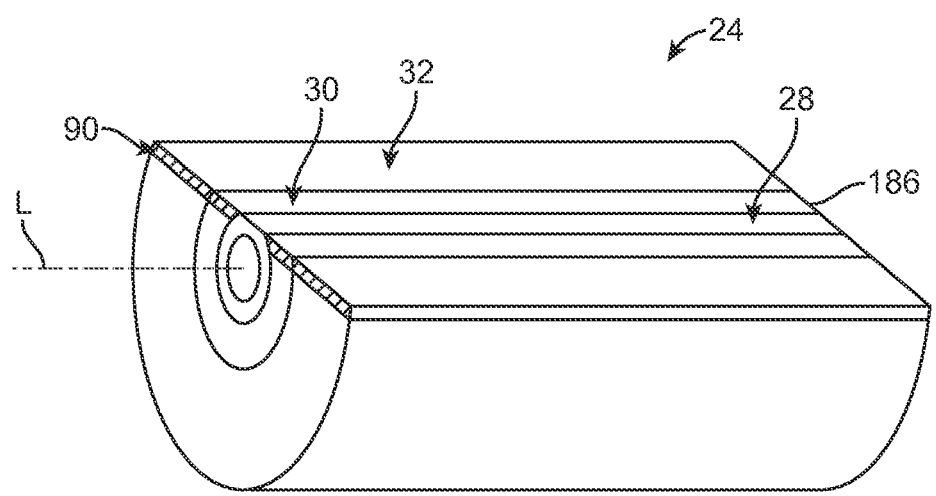

Upon hardening of the potting compound 170, the precursor bundle assembly 160 has now transitioned into an intermediate core assembly 180 as shown in FIG. 9A. The intermediate core assembly 180 is then cut lengthwise within a thickness of the potting compound 170. For example, FIG. 9A illustrates a cut line at 182; the cut line 182 is "within" a thickness of the potting compound 170 (represented by cross-hatching in FIGS. 9A and 9B), for example in close proximity to the potting compound edge 172. The cut can be formed in various manners, and in some embodiments is akin to a guillotine cut. Regardless, a cut portion 184 of the intermediate core assembly 180 is removed, resulting in the final core assembly 24 of FIG. 9B (it being understood that the core assembly 24 is illustrated in simplified form in FIG. 9B). A face 186 of the core assembly 24 corresponds with the cut line 182 (FIG. 9A), and is substantially parallel to (e.g., within 10% of a truly parallel relationship) the longitudinal axis L. While the cut line 182 (and thus the face 186) is shown as being a single, planar cut, in other embodiments, multiple cuts can be made to generate the face 186 as being non-planar. The cutting operation "completes" the heat exchanger bundle 30 (i.e., transitions the heat exchanger precursor bundle 130 (FIG. 6D) into the final heat exchanger bundle 30), the oxygenator bundle 32 and the potting structure 90 (represented by stippling in FIG. 9B), with lumens (not individually shown) of the heat exchanger bundle 30 and the oxygenator bundle 32 being exposed at the face 186, and spatially maintained by the potting structure 90.

Figure 10:
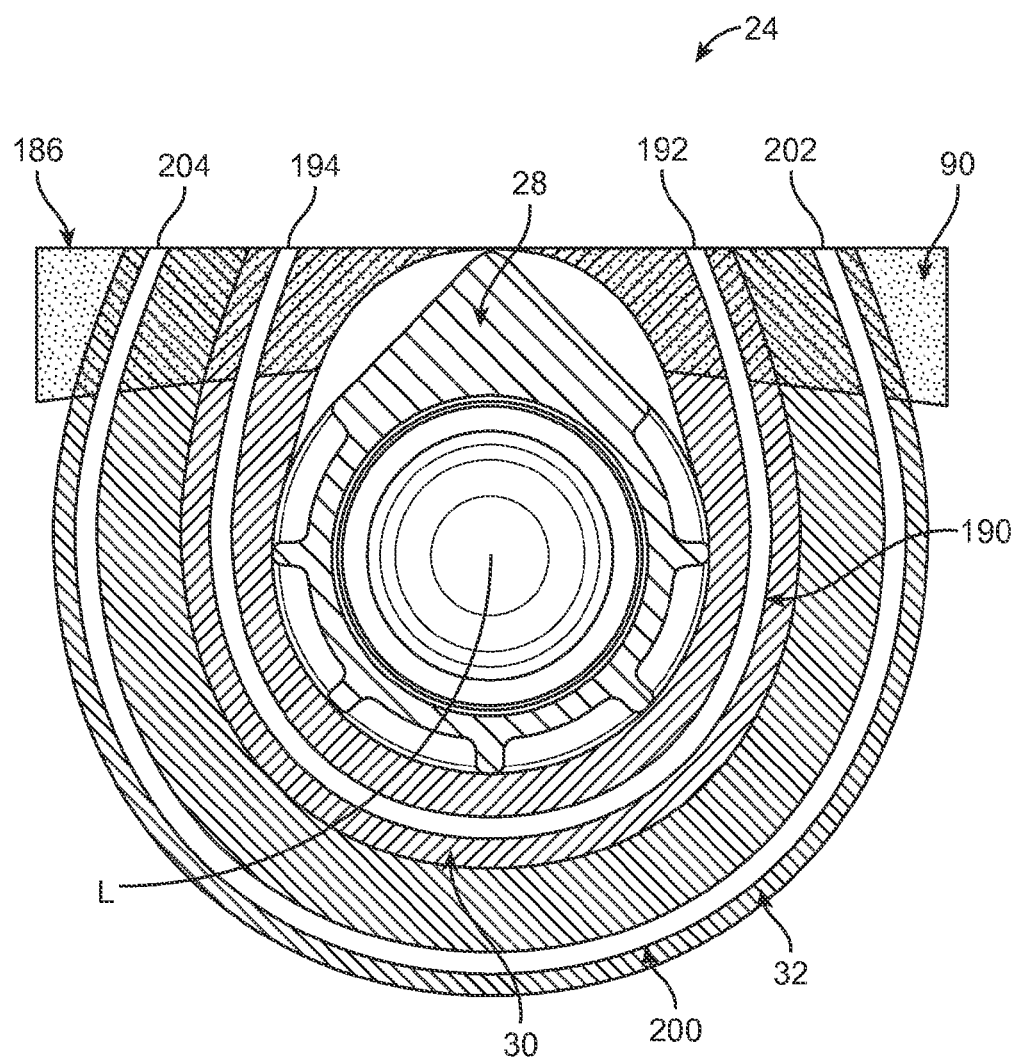
FIG. 10 is a cross-sectional view of the core assembly of FIG. 2A and illustrates a heat transfer capillary tube and a gas exchange fiber in exaggerated form.

The above-described cutting process converts the continuous heat transfer tubing 120 (FIG. 6B) into a plurality of heat transfer capillary tubes 190 one of which is depicted in simplified, exaggerated form in FIG. 10. Each of the heat transfer capillary tubes 190 of the heat exchanger bundle 30 extends between opposing, first and second ends 192, 194, and is partially wound about the longitudinal axis L. More particularly, a lumen of each of the heat transfer capillary tubes 190 is open at the corresponding ends 192, 194 and is schematically represented in FIG. 10 as defining an arc relative to the longitudinal axis L, with an arc angle of the heat transfer capillary tubes 190 being less than 360 degrees. In some embodiments, the arc angle is at least 180 degrees, in other embodiments is at least 200 degrees, in yet other embodiments is at least 220 degrees, and in yet other embodiments is at least 240 degrees. The first and second ends 192, 194 are located in the face 186 at opposite sides of the longitudinal axis L.

The cutting process similarly converts or transitions the continuous gas exchange tubing 140 (FIG. 7A) into a plurality of gas exchange fibers 200, one of which is shown in simplified, exaggerated form in FIG. 10. The gas exchange fibers 200 of the oxygenator bundle 32 each terminate at opposing, first and second ends 202, 204 that are maintained at the face 186. Each of the gas exchange fibers 200 defines an arc about the longitudinal axis L, with an arc angle of each of the gas exchange fibers 200 being less than 360 degrees. In some embodiments, the arc angle is at least 180 degrees, in other embodiments is at least 200 degrees, in yet other embodiments is at least 220 degrees, and in yet other embodiments is at least 240 degrees. The first and second ends 202, 204 are located at opposite sides of the longitudinal axis L.

Figure 11A:
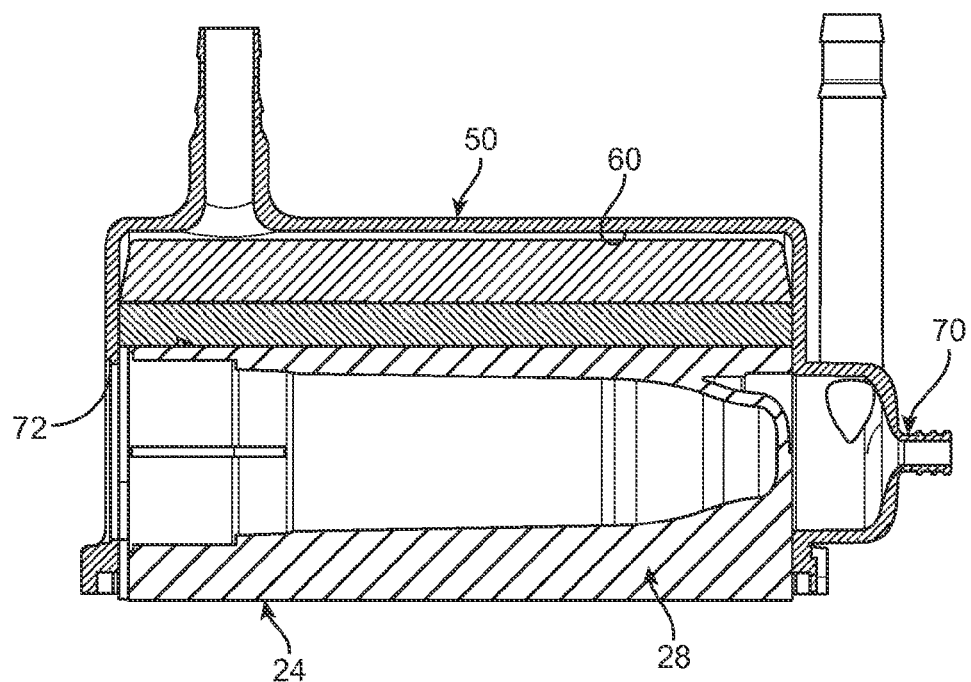
FIGS. 11A-11C illustrate assembly of the apparatus of FIG. 2A.
Figure 11B:
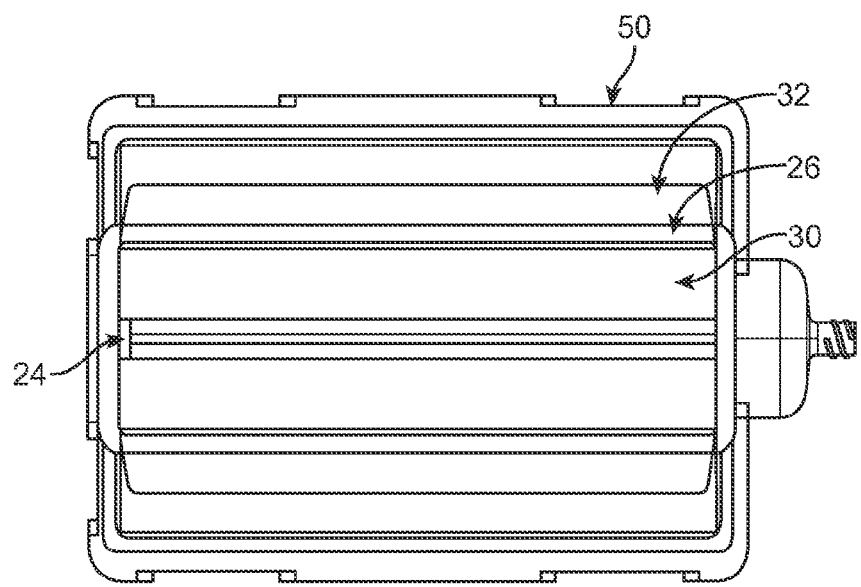
Figure 11C:
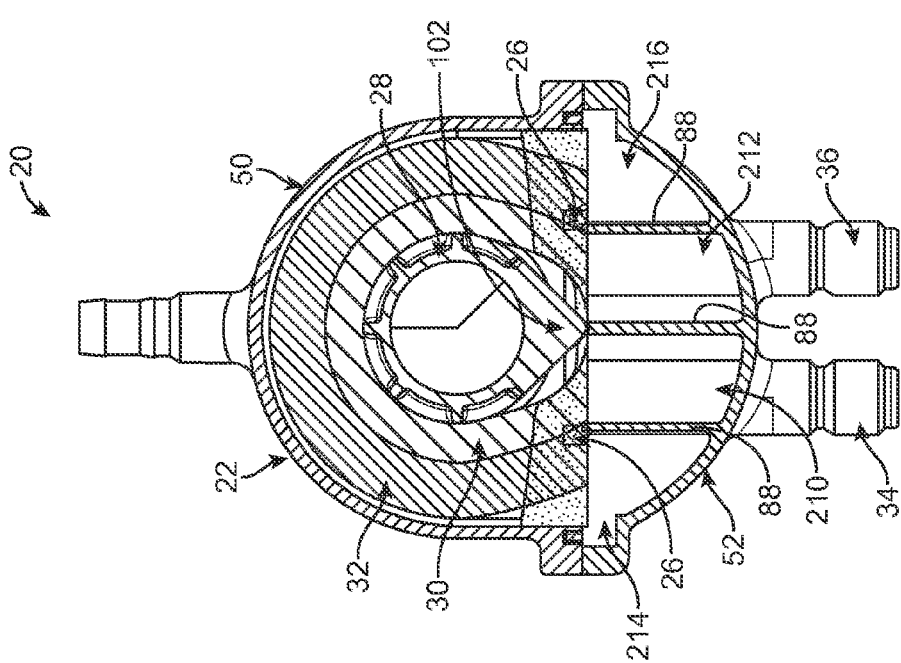

Returning to FIG. 2A, the so-formed core assembly 24 is then assembled within the housing 22. For example, as shown in FIG. 11A, the core assembly 24 is located within the chamber 60 of the first housing portion 50, with the core 28 being generally aligned with the air purge port 70. Where provided, the hole 72 is also aligned with the core 28. While the core 28 can have a generally hollow construction as described above, the hole 72 is sealed relative to the chamber 60 via the core 28. The separator 26 is then mounted to the core assembly 24, fluidly separating the heat exchanger bundle 30 from the oxygenator bundle 32 as shown in FIG. 11B. Finally, the second housing portion 52 is mounted to the first housing portion 50 as reflected in FIG. 11C. Where provided, the internal support walls 88 abut the separator 26 and the shoulder region 102 of the core 28 as shown. With this arrangement, the potting structure 90 is fitted against the first housing portion side wall 62. A sealed heat transfer inlet region 210 and a sealed heat transfer outlet region 212 are established. Similarly, sealed gas inlet and outlet regions 214, 216 are also created. An additional, single seal (not shown) can be formed between the potting structure 90 and the housing 22 (or elsewhere) that isolates the core 28 from the heat transfer inlet and outlet regions 210, 212.

Figure 12:
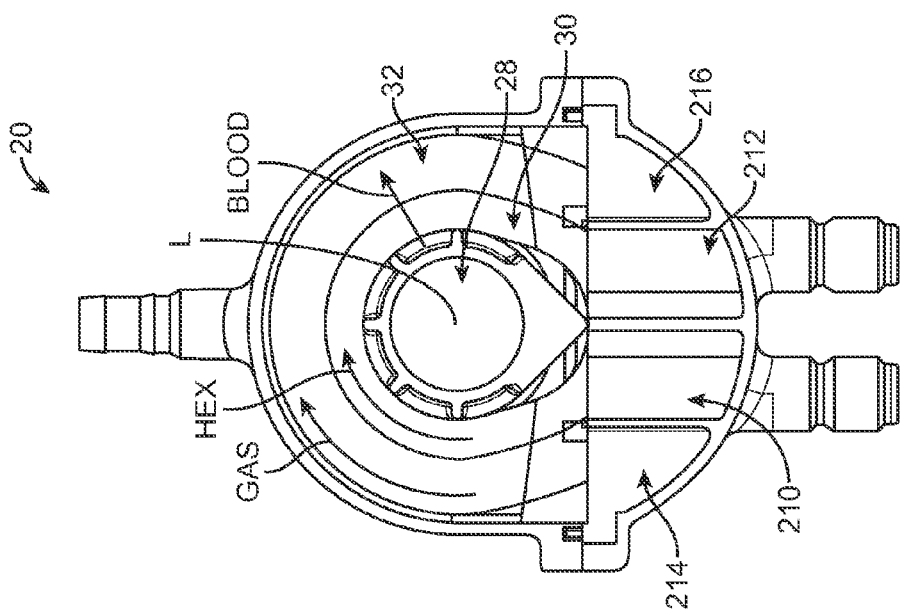
FIG. 12 is a cross-sectional view of the apparatus of FIG. 2A upon final assembly and designating various flow paths during use.

During use of the integrated apparatus 20 and as shown in FIG. 12, incoming blood flow is distributed in a generally radial direction from the core 28 (represented by the line "BLOOD" in FIG. 12). As the blood flow traverses through the heat exchanger bundle 30, a temperature of the blood is adjusted via the flow of a heat transfer fluid (e.g., water) through the heat transfer capillary tubes (not shown individually) of the heat exchanger bundle 30. In this regard, the heat transfer fluid enters the heat exchange capillary tubes at the heat transfer inlet region 210, and exits at the heat transfer outlet region 212, traversing an arc angle less than 360 degrees. The heat transfer fluid flow path is represented by the arrow labeled "HEX". The blood flow path continues from the heat exchanger bundle 30 in a generally radial direction through oxygenator bundle 32. Oxygenation (and carbon dioxide removal) of the blood occurs as the blood interfaces with the gas exchange fibers (not shown individually) of the oxygenator bundle 32. In this regard, the gas exchange medium enters the gas exchange fibers at the gas exchange inlet region 214 and exits at the gas exchange outlet region 216, traversing an arc angle less than 360 degrees. A flow path of the gas exchange medium is represented by an arrow labeled "GAS" in FIG. 12.

Commensurate with the above descriptions, the heat transfer fluid flow path is relatively short as compared to conventional designs. The heat transfer fluid traverses through each of the heat exchange capillary tubes along a flow path of less than 360 degrees (relative to the longitudinal axis L) before exiting the apparatus 20, and thus has a relatively short dwell time. As a result, as "new" heat transfer fluid is constantly flowing through the heat exchanger bundle 30, the heat exchange efficiency is optimized. Similarly, the gas exchange medium travels only a short distance, traversing through each of the gas exchange fibers along a flow path of less than 360 degrees relative to the longitudinal axis L. This equates to a decrease in gas residence time, likely reducing the amount of gas exchange fibers required to effectuate desired gas exchange levels. The single seal (not shown) described above prevents co-mingling of the heat transfer fluid with the blood. Unlike other designs in which the blood and heat transfer chambers are directly adjacent, the combination apparatuses of the present disclosure effectively move the heat transfer chamber away from the blood chamber so that only a single seal is required.

Although the core assembly 24 has been described as incorporating similarly formed heat exchanger bundle and oxygenator bundle components (i.e., forming the heat exchanger precursor bundle and the oxygenator precursor bundle followed by potting and cutting), in other embodiments the core assembly 24 can consist of the core 28 and the heat exchanger bundle 30 as manufactured by the above-described techniques, with the oxygenator bundle 32 being a separately formed component that may or may not be directly assembled onto the heat exchanger bundle 30. Further, location of the various ports and resultant flow paths can assume a variety of other formats in other embodiments.

The integrated perfusion apparatuses and methods of manufacture of the present disclosure provide a marked improvement over previous designs. The heat exchange fluid and optionally the gas exchange medium traverse a relatively shortened path as compared to previous designs, thus improving overall efficiencies. Further, with the partial radial construction of the core assembly, only two housing segments are required in some embodiments thus reducing overall costs. Only a single potting structure is required, and thus further relieves costs and manufacturing steps.

Although the present disclosure has been described with reference to preferred embodiments, workers skilled in the art will recognize that changes can be made in form and detail without departing from the spirit and scope of the present disclosure.

What is claimed is:

1. An apparatus for oxygenating and controlling temperature of blood in an extracorporeal circuit, the apparatus comprising:
   a housing providing a blood inlet and a blood outlet;
   a core disposed within the housing and defining a longitudinal axis, a first terminal side, and a second terminal side opposite the first terminal side;
   a heat exchanger bundle including a plurality of heat transfer capillary tubes arranged directly over the core, each of the heat transfer capillary tubes terminating at opposing, first and second ends and extending about the core to define an arc relative to the longitudinal axis, the arc having an arc angle of less than 360 degrees, wherein both of the first and second ends of at least one of the heat transfer capillary tubes are closer to the first terminal side than the second terminal side; and
   an oxygenator bundle including a plurality of gas exchange fibers arranged directly over the heat exchanger bundle;

wherein the apparatus is configured to establish a blood flow path from the blood inlet to the blood outlet passing radially through the heat exchanger bundle and the oxygenator bundle.

2. The apparatus of claim 1, further comprising a potting structure encompassing the first end of each of the heat transfer capillary tubes, and further wherein a face of the potting structure is arranged in a plane substantially parallel with the longitudinal axis.

3. The apparatus of claim 2, wherein the potting structure encompasses the second end of each of the heat transfer capillary tubes.

4. The apparatus of claim 3, wherein the potting structure further encompasses first and second opposing ends of each of the gas exchange fibers.

5. The apparatus of claim 1, wherein the core is configured to direct blood flow from the blood inlet radially outward to the heat exchanger bundle.

6. The apparatus of claim 1, wherein the plurality of heat transfer capillary tubes each include a lumen to which a heat exchange fluid can be supplied in order to control the temperature of blood that can move between the plurality of heat transfer capillary tubes.

7. The apparatus of claim 6, wherein the plurality of heat transfer capillary tubes are arranged such that movement of the heat exchange fluid through the plurality of heat transfer elements is substantially transverse to the radially outward direction that blood can move between the plurality of heat transfer capillary tubes.

8. The apparatus of claim 1, wherein the plurality of gas exchange fibers each comprise a lumen through which an oxygen-containing gas medium can be supplied in order to oxygenate blood that can move between the plurality of gas exchange fibers.

9. The apparatus of claim 8, wherein the plurality of gas exchange fibers are arranged such that the movement of the gas medium through the plurality of gas exchange fibers is substantially transverse to the radially outward direction that blood can move between the plurality of gas exchange fibers.

10. The apparatus of claim 1, wherein each of the gas exchange fibers terminate at opposing, first and second ends and extend about the heat exchanger bundle to define an arc relative to the longitudinal axis, the arc of each of the gas exchange fibers having an arc angle of less than 360 degrees.

11. The apparatus of claim 1, wherein the arc angle of each of the heat transfer capillary tubes is at least 180 degrees.

12. A method of making an apparatus for oxygenating and controlling temperature of blood in an extracorporeal circuit, the method comprising:
  winding at least one continuous heat transfer tubing about a core defining a longitudinal axis to define a heat exchanger precursor bundle;
  applying a potting compound to a portion of the heat exchanger precursor bundle to provide an intermediate core assembly, the potting compound solidifying to form a potting structure defining an internal face extending through the heat exchanger precursor bundle in a plane substantially parallel with the longitudinal axis;
  cutting the intermediate core assembly along a cut line passing through the potting structure to define a core assembly having a cut face, wherein the step of cutting: transforms the heat transfer tubing into a plurality of heat transfer capillary tubes each terminating at opposing, first and second ends and extending about the core to define an arc relative to the longitudinal axis, the arc having an arc angle of less than 360 degrees, the plurality of heat transfer capillary tubes forming a heat exchanger bundle,
  forming an oxygenator bundle as part of the core assembly and including a plurality of gas exchange fibers arranged directly over the heat exchanger bundle; and
  disposing the core assembly within a housing providing a blood inlet and a blood outlet.

13. The method of claim 12, wherein the first and second ends of each of the heat transfer capillary tubes fluidly open at the cut face.

14. The method of claim 12, wherein the cut face defines a plane substantially parallel with the longitudinal axis.

15. The method of claim 12, wherein the step of disposing the core assembly within a housing includes fluidly connecting the core with the blood inlet such that blood from the blood inlet flows radially outward to the heat exchanger bundle.

16. The method of claim 12, wherein the housing includes a first housing portion and a second housing portion, the first housing portion carrying the blood inlet and the blood outlet, the second housing portion providing a heat transfer inlet, a heat transfer outlet, a gas exchange inlet, and a gas exchange outlet, and further wherein the step of disposing the core assembly within the housing includes assembling the first housing portion to the second housing portion to complete the apparatus.

17. The method of claim 15, wherein following the step of assembling the first housing portion to the second housing portion, the heat transfer inlet is fluidly open to the first end of each of the heat transfer capillary tubes, the heat transfer outlet is fluidly open to the second end of each of the heat transfer capillary tubes, the gas exchange inlet is fluidly open to a first end of each of the gas exchange fibers, and the gas exchange outlet is fluidly open to a second end of each of the gas exchange fibers.

18. The method of claim 12, wherein the step of forming an oxygenator includes:
  winding at least one continuous gas exchange tubing about the heat exchanger bundle to define an oxygenator precursor bundle prior to the step of applying a potting compound.

19. The method of claim 18, wherein the step of applying a potting compound includes applying the compound to a portion of the oxygenator precursor bundle, and further wherein the intermediate core assembly includes the oxygenator precursor bundle.

20. The method of claim 19, wherein the step of cutting the intermediate core assembly transforms the gas exchange tubing into the plurality of gas exchange fibers each terminating at opposing, first and second ends and extending about the heat exchanger bundle to define an arc relative to the longitudinal axis, the arc of each of the gas exchange fibers having an arc angle of less than 360 degrees.

* * * * *